US006463314B1

(12) United States Patent
Haruna (10) Patent No.: US 6,463,314 B1
(45) Date of Patent: Oct. 8, 2002

(54) NANOSECOND GATE SPECTROSCOPIC DIAGNOSTIC DEVICE (75) Inventor: Masamitsu Haruna, Toyonaka (JP)

(73) Assignee: Japan Science and Technology Corporation (JP)

( * ) Notice: Subject to any disclaimer, the term of this patent is extended or adjusted under 35 U.S.C. 154(b) by 0 days.

(21) Appl. No.: 09/423,354

(22) PCT Filed: Feb. 19, 1999

(86) PCT No.: PCT/JP99/00733

§ 371 (c)(1),
(2), (4) Date: Nov. 23, 1999

(87) PCT Pub. No.: WO99/49300

PCT Pub. Date: Sep. 30, 1999

(30) Foreign Application Priority Data

Mar. 24, 1998 (JP) .......................................... 10-075359

(51) Int. Cl.⁷ ............................................... A61B 5/00
(52) U.S. Cl. ......................... 600/407; 600/473; 600/476
(58) Field of Search ............................... 600/407, 309, 600/310, 473, 475, 476, 477; 356/311, 316, 317, 318, 319, 320, 326, 330, 334

(56) References Cited

U.S. PATENT DOCUMENTS

| 3,768,908 | A | * | 10/1973 | Zaromb | 356/103 |
| 4,802,761 | A | * | 2/1989 | Bowen et al. | 356/301 |
| 5,033,853 | A | * | 7/1991 | Frangineas | 356/346 |
| 5,608,520 | A | * | 3/1997 | Fleming | 356/318 |
| 5,720,894 | A | * | 2/1998 | Neev et al. | 216/65 |
| 5,842,995 | A | * | 12/1998 | Mahadevan-Jansen et al. | 600/473 |
| 5,873,875 | A | * | 2/1999 | Altshuler | 606/10 |
| 6,008,896 | A | * | 12/1999 | Sabsabi et al. | 356/318 |
| 6,008,897 | A | * | 12/1999 | Sabsabi et al. | 356/318 |
| 6,156,030 | A | * | 12/2000 | Neev | 606/105 |

FOREIGN PATENT DOCUMENTS

| JP | 1-321340 A | 12/1989 |
| JP | 6-300694 A | 10/1994 |

OTHER PUBLICATIONS

Denshi Jouhou Tsuushin Gakkai vol. 96, No. 429 (Japan), IEICE, pp. 9–16. (1996).

* cited by examiner

Primary Examiner—Marvin M. Lateef
Assistant Examiner—Eleni Mantis Mercader
(74) Attorney, Agent, or Firm—Lorusso & Loud (57) ABSTRACT A diagnosis apparatus comprises a shutter (11) disposed between a light source (1) and a lens (12) opposed to biological tissue (13); a multi-channel spectrometer (polychromator) (16) for detecting a light emitting plume (14); a photodetector (5) for detecting a portion of a laser pulse from the light source (1); an oscilloscope (6) which monitors an output from the photodetector (5) to thereby measure a delay time of a gate trigger pulse supplied to a high-speed gate image intensifier (17); a pulse generator (8) capable of independently and freely adjusting the delay times of two output pulses in synchronization with the laser pulse; a gate controller (7) connected to the pulse generator (8) and the oscilloscope (6); the high-speed gate image intensifier (17) intensifying and imaging the output of the multi-channel spectrometer (16) whose gate is opened by the gate controller (7) over a period on the order of nanosecond; a CCD camera (9) capturing an output image from the high-speed gate image intensifier (17); and a data-processing apparatus comprising a frame image data storage (10A) which inputs spectroscopic image data of one frame from the CCD camera (9) as a time-series analog signal, and converts the analog signal to a digital signal for transmission to a computer (10).

11 Claims, 9 Drawing Sheets

WAVELENGTH (nm)

NANOSECOND GATE SPECTROSCOPIC DIAGNOSTIC DEVICE

TECHNICAL FIELD

The present invention relates to a nanosecond time-gate spectroscopic diagnosis apparatus.

BACKGROUND ART

Conventionally, in relation to the above-described field, the following literature have been known.

(1) Medical Equipment Encyclopedia Edition Committee, ed., "1987–88 Medical Equipment Encyclopedia," pp. 426–436, Sangyo Chosakai (2) "Encyclopedia of Medical Sciences," pp. 46–50, Kodansha (3) Takuzo Sato, "From Laser CD Player to X-ray Laser," pp. 146–170, Denki Shoin (1987)

(4) Harufumi Kato, Hideki Yamamoto, and Toshimitsu Hiyoshi, "Therapeutic Effect on Cancer by Photosensitive Substances," O plus E, No. 160, pp. 83–88 (1993)

(5) Yusaku Shimaoka, Masato Ohmi, and Masamitsu Haruna, "Nanosecond Stroboscopic Microscope for Laser Ablation of Biological Tissue," The Institute of Electronics, Information and Communication Engineers, ME and Bio Cybernetics Study Group, Technical Report of IEICE MBE96-93 (1996)

(6) Yusaku Shimaoka, Mitsuo Nakamura, Masato Ohmi, and Masamitsu Haruna, "Nanosecond Stroboscopic Microscope for Laser Ablation of Biological Tissue," Conference on Laser & Electro Optics/Pacific Rim (CLEO/PR'97), Paper FF3, Technical Digest pp. 261–262, Makuhari, Chiba, 1997

Conventionally, in actual medical treatment facilities, infrared $CO_2$ lasers and Nd:YAG lasers, serving as laser scalpels, have been used for incision and coagulation in surgical operations (see literature (1) and (2)).

Laser-induced fluorescence analysis (see the above-describe literature (3) and (4)) has been continually studied as an effective diagnosis method. Henceforth, improvement and utilization of a laser-induced biological reaction as a leading medical technique require collection and accumulation of detailed experimental data, including variations with time of a reaction state in the vicinity of the surface of biological tissue caused by irradiation with a laser pulse, and compositions of substances scattering from the surface, as obtained from analysis.

DISCLOSURE OF THE INVENTION

Physical phenomena such as laser ablation of biological tissue and fluorescence generation therefrom occur within a period on the order of nanosecond or less, as is the case of physical phenomena in inorganic substances (see the above-describe literature (3) and (4)). Therefore, spectroscopic analysis of these phenomena requires an optical measurement techniques with a time resolution on the order of nanosecond. Laser ablation of biological tissue refers to a phenomenon by which biological tissue decomposes thermally or photochemically by irradiation with a laser pulse and evaporates instantly.

The present inventors have already developed a nanosecond stroboscopic microscopy system and have performed dynamic analysis of laser ablation of biological tissue (see the above-described literature (5) and (6)). In the system, through spectral analysis of a light emitting plume, the composition of a biological tissue sample can be elucidated, enabling discrimination between normal and lesioned portions of the tissue. Therefore, plume spectral analysis, along with the fluorometric analysis technique, is expected to become a key technology for optical biopsy.

In stroboscopic analysis using a monochromator (see the above-described literature (6)), which is one of several emission spectral analysis techniques, measurement at one particular wavelength can be performed through irradiation with a single laser pulse. Therefore, stroboscopic analysis requires a long time for measurement of plume emission spectra, resulting in damage to the sample being analyzed, and application of such an analysis to a clinical setting is considered to be problematic.

In view of the foregoing, the object of the present invention is to provide a nanosecond time-gate spectroscopic diagnosis apparatus which performs instant spectroscopic analysis of a light emitting plume through irradiation of a biological tissue sample with a single laser pulse, by use of a photo multi-channel analyzer comprising a high-speed gate image intensifier having a gate width on the order of nanosecond.

To achieve the above object, the present invention provides the following:

(1) A nanosecond time-gate spectroscopic diagnosis apparatus wherein a laser pulse from a light source is radiated onto biological tissue in a focused manner, a light emitting plume (a spindle-shaped light emitting substance) generated from the surface of the tissue due to laser ablation is spectroscopically measured at a time gate on the order of nanosecond, and the composition of the tissue is analyzed on the basis of the plume spectra, to thereby diagnose lesion or anomaly of the tissue, the apparatus comprising: a shutter disposed between the light source and a lens opposed to biological tissue; a multi-channel spectrometer (polychromator) for detecting the light emitting plume; a photodetector for detecting a portion of the laser pulse from the light source; an oscilloscope which monitors an output from the photodetector to thereby measure a delay time of a gate trigger pulse supplied to a high-speed gate image intensifier; a pulse generator capable of independently and freely adjusting the delay time of two output pulses in synchronization with the laser pulse; a gate controller connected to the pulse generator and the oscilloscope; the high-speed gate image intensifier, intensifying and imaging the output of the multi-channel spectrometer, whose gate is opened over a time slot on the order of nanosecond by the gate controller; a CCD camera capturing an output image from the high-speed gate image intensifier; and a data-processing apparatus comprising a frame image data storage (frame grabber) which inputs spectroscopic image data of one frame from the CCD camera as a time-series analog signal, and converts the analog signal to a digital signal for transmission to a computer.

(2) A nanosecond time-gate spectroscopic diagnosis apparatus described in (1) above, wherein biological tissue is evaporated and excited by laser ablation, and spectra of a light emitting plume generated due to evaporation and excitation are detected at intervals on the order of nanosecond.

(3) A nanosecond time-gate spectroscopic diagnosis apparatus described in (1) above, wherein the light source is a laser light source which generates a nanosecond laser pulse within the UV range, the visible range, or the IR range.

(4) A nanosecond time-gate spectroscopic diagnosis apparatus described in (1) above, wherein the laser beam source is a flash-lamp-excited or semiconductor-laser-excited Q-switched Nd:YAG laser, or a semiconductor-laser-excited full-solid Q-switched Nd:YAG laser.

(5) A nanosecond time-gate spectroscopic diagnosis apparatus described in (1) above, wherein a laser beam from the light source includes light having a wavelength longer than the wavelength of a light emitting plume to be detected.

(6) A nanosecond time-gate spectroscopic diagnosis apparatus described in (1) above, wherein a shutter is disposed between the light source and the biological tissue, whereby a spectroscopic diagnosis of very low invasiveness is enabled through irradiation of the biological tissue with a single laser pulse.

(7) A nanosecond time-gate spectroscopic diagnosis apparatus described in (1) above, wherein the multi-channel spectrometer has a structure such that a light beam entering through an inlet slit is split, by use of a plurality of gratings, into a plurality of light beams corresponding to different wavelengths, and light beams having wavelengths within a particular range exit simultaneously from an exit opening at different angles.

(8) A nanosecond time-gate spectroscopic diagnosis apparatus described in (7) above, wherein the density of grating grooves of the grating is selectively set to 150/mm, 300/mm, 600/mm, or 1200/mm.

(9) A nanosecond time-gate spectroscopic diagnosis apparatus described in (7) above, wherein light beams having wavelengths within a particular range and exiting from the multi-channel spectrometer forms an image on pixels of the CCD camera.

(10) A nanosecond time-gate spectroscopic diagnosis apparatus described in (1) above, further comprising means for synchronizing operation of the high-speed gate image intensifier and operation of the CCD camera with a trigger pulse from the light source.

(11) A nanosecond time-gate spectroscopic diagnosis apparatus described in (1) above, wherein the biological tissue is biological hard tissue such as hair, a nail, or a tooth.

(12) A nanosecond time-gate spectroscopic diagnosis apparatus described in (1) above, wherein the biological tissue is biological soft tissue such as a vascular wall or subepidermal tissue.

BEST MODE FOR CARRYING OUT THE INVENTION

An embodiment of the present invention will next be described in detail.

The present invention provides a nanosecond time-gate spectroscopic apparatus using laser ablation of biological tissue. The characteristics and functions of a laser beam source; a system for pulse generation, pulse synchronization, delay control; a time-gate spectroscopic system; and a spectroscopic image processing system in the apparatus are described below. In addition, there is given an explanation of a method by which the gate width for measurement of spectra was determined.

Figure 1:
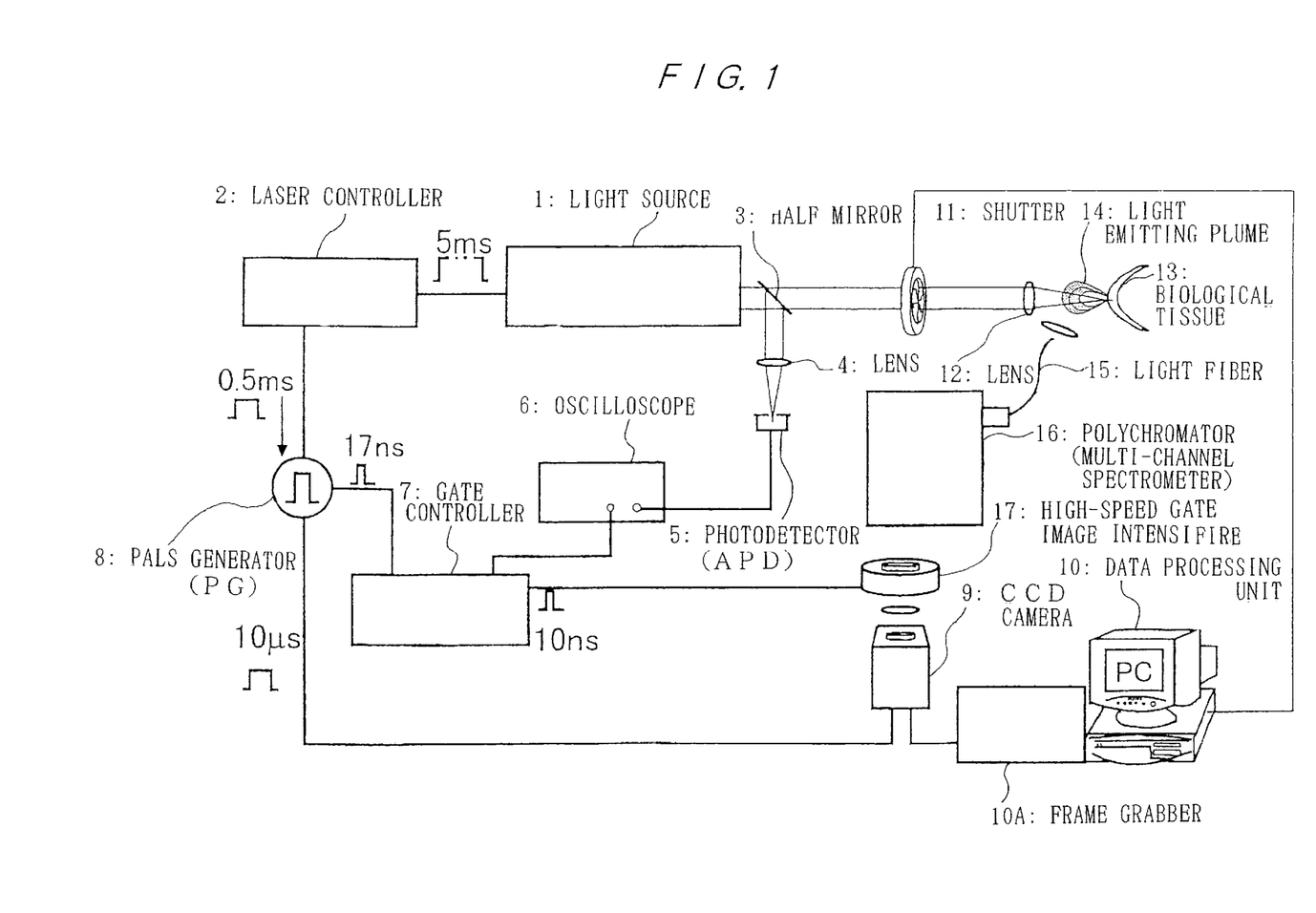
FIG. 1 is a diagram showing the structure of a nanosecond time-gate spectroscopic system according to an embodiment of the present invention.

FIG. 1 is a diagram showing the structure of a nanosecond time-gate spectroscopic system according to an embodiment of the present invention. In FIG. 1, reference numeral 1 denotes a light source (for example, a flash-lamp-excited or semiconductor-laser-excited Q-switched Nd:YAG laser, or a semiconductor-laser-excited full-solid Q-switched Nd:YAG laser); 2 denotes a laser controller connected to the light source 1; 3 denotes a half mirror; 4 and 12 denote lenses; 5 denotes a photodetector (avalanche photo diode: APD); 6 denotes an oscilloscope for measurement/monitoring of a gate-pulse delay time; 7 denotes a gate controller for a high-speed gate image intensifier; 8 denotes a pulse generator (PG); 9 denotes a CCD camera; 10 denotes a data processing unit having an image processing function (personal computer: PC); 10A denotes a frame image data storage (a frame grabber); 11 denotes a shutter; 13 denotes biological tissue (e.g. a human nail); 14 denotes a light emitting plume; 15 denotes an optical fiber; 16 denotes a polychromator (multi-channel spectrometer); and 17 denotes a high-speed gate image intensifier.

The operation of the nanosecond time-gate spectroscopic system according to the embodiment of the present invention will next be described.

A single laser pulse (pulse width: 10–90 ns) from the light source 1 (e.g., a Q-switched Nd:YAG laser) is caused to pass through the shutter 11 and is radiated onto the biological tissue (ex. a human nail) 13 in a focused manner. As a result, a very small amount of the tissue (diameter: about 50 μm, depth: about a few microns) is evaporated (ablated), and thus an exited state is created, so that a light-emitting plume (a spindle-shaped light-emitting substance) 14 is generated.

Immediately after the laser irradiation, water evaporates primarily from the vicinity of the surface of the biological tissue (human nail) 13, and a bright spindel-shaped emission plume (hereinafter referred to as a leading plume) is generated and grown. In addition, about 100 ns after the laser irradiation, the surface of the tissue (human nail) exfoliates, so that a "chasing plume" is generated. The chasing plume is an evaporated and excited substance containing biological tissue components to be analyzed through measurement of emission spectra.

Therefore, in order to measure emission spectra of the above-described chasing plume, the following procedure is performed. A portion of the laser pulse from the light source 1 is detected by use of the photodetector (avalanche photo diode: APD) 5. While the time when the pulse is detected is used as a reference point, a delay time of a gate trigger pulse output from the pulse generator 8 is measured and set to a predetermined value within the range of 300–400 ns, by use of the oscilloscope 6. Further, the gate controller 7 for the high-speed gate image intensifier 17 is operated in order to open the gate of the high-speed gate image intensifier 17 over a time slot of 10 ns. With this operation, the high-speed gate image intensifier 17 fetches a 10-nanosecond time-gate spectroscopic image of the emission spectrum of the chasing plume, which is detected by use of the optical fiber 15 and the polychromator 16.

Furthermore, an image (spectroscopic image data) output from the intensifier 17 is captured by use of the CCD camera 9, and the data is converted to a time-series signal pulse. Subsequently, via the frame grabber 10A (frame image data storage), the signal data are transmitted, for processing, into a data processing apparatus comprising a personal computer 10. The frame grabber 10A accumulates/stores, in predetermined memory, data for one frame of the CCD camera or a television as a time-series signal, converts the time-series signal (analog signal) to an 8-bit or 10-bit digital signal, and transmits the digital signal to the computer. Depending on the memory capacity, typically, image data for 10 or more frames can be accumulated/stored simultaneously, and when necessary, a desired frame data set is fed to the computer.

In this system, photo-spectra within a range of 300–900 nm can be measured and displayed at a wavelength resolution of 1 nm (measurement is performed for each of four sub-ranges defined in the range).

As described above, in the nanosecond time-gate spectroscopic system, radiation of a single laser pulse enables spectroscopic analysis of the light-emitting plume of an evaporated substance, to thereby enable optical diagnosis in a substantially noninvasive manner.

Particularly, ions of a metal such as Ca, Na, or K, which have a high ionization tendency, can be effectively detected.

Therefore, for example, the system enables diagnosis of osteoporosis in an elderly person through measurement of the Ca content of his/her nail or hair.

As described above, the present invention provides a new technique and an apparatus which evaporates biological tissue in a very small amount by use of a laser pulse serving as a probe in order to diagnose lesion of the tissue. The technique and apparatus have high potential of becoming a key technology and apparatus for optical biopsy, together with the conventional fluorescence diagnosis technique.

Further, a semiconductor laser (LD)-excited full-solid Nd:YAG laser may be used in order to provide a diagnosis apparatus of reduced size.

The respective portions of the nanosecond time-gate spectroscopic system will next be described in more detail.

A Q-switched Nd:YAG laser is used for generating a laser beam, having a fundamental wavelength of 1064 nm. The laser beam is focused by use of the lens (focal length f=100 mm) 12 and is radiated onto the biological tissue (human nail) 13, to thereby ablate the tissue.

In the system, the shutter 11 is interposed between the light source 1 and the lens 12, and is controlled such that the tissue (human nail) 13 is irradiated with a single laser pulse and is thereby ablated when the shutter 11 is opened. A light beam emitted from the light-emitting plume 14 is caused to enter the polychromator 16 via the optical fiber 15.

The incident light beam is then split into a plurality of light beams by a grating provided in the polychromator 16, and the split light beams exit the polychromator 16. The split light beams are intensified by the high-speed gate image intensifier 17, so that an image is formed on a fluorescence surface thereof. The thus-formed fluorescence image is captured by the CCD camera 9 as a spectroscopic image. Subsequently, image data output from the CCD camera are input to the frame grabber 10A as a time-series signal, and the analog signal is converted to a digital signal for data processing.

Since the spectroscopic image exiting from the polychromator 16 extends laterally (in a direction corresponding to light wavelength), in order to capture the image at a time-gate (shutter speed) of 10 ns, the image signal must be amplified or intensified by a factor of 1,000 to 1,000,000. For example, an image intensifier C4078-01X (product of HAMAMATSU PHOTONICS K. K., minimum gate width (shutter speed): 3 ns) may be used as the high-speed gate image intensifier 17.

In the system, Spectra Pro-300i, Model SP-306 (product of Acton Research) is used as the polychromator (multi-channel spectrometer) 16. The polychromator comprises three types of gratings, and can perform measurement within a wavelength range of 300–900 nm at a resolution of 1 nm.

Figure 2:
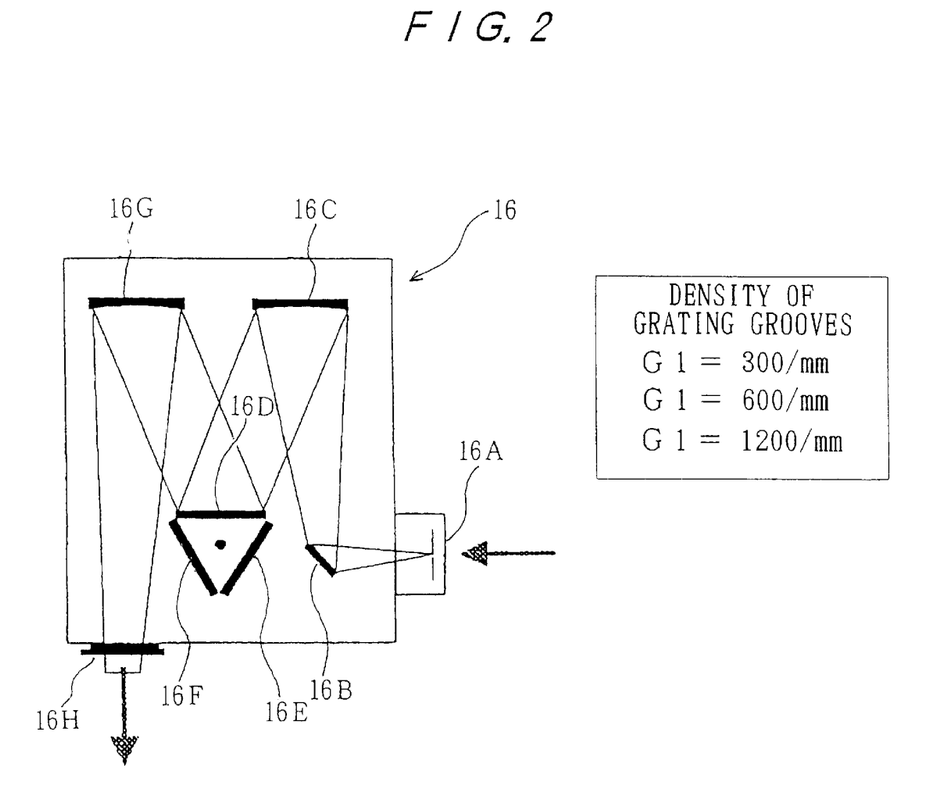
FIG. 2 is a schematic diagram showing the structure of a multi-channel spectrometer (polychromator) according to the present invention.

FIG. 2 is a schematic diagram showing the structure of the polychromator used in the present invention.

As shown in FIG. 2, by means of gratings 16D–16F, a light beam entering from an entrance slit 16A is split into a plurality of light beams (spectral components) corresponding to different wavelengths. Reference numerals 16B, 16C, and 16G each denote a reflecting mirror. Spectral components within a predetermined wavelength range simultaneously exit from an exit opening 16H at different angles, and these spectral components are detected at different position s on the CCD camera.

A processing system for spectroscopic picture image will next be described.

The split light beams (spectral components) split by means of the gratings 16D–16F in the polychromator 16 form a spectroscopic image on the CDD camera 9. In the spectroscopic image, the horizontal axis corresponds to wavelength.

The thus-obtained time-series data are input to a personal computer and subjected to processing.

Figure 3A:
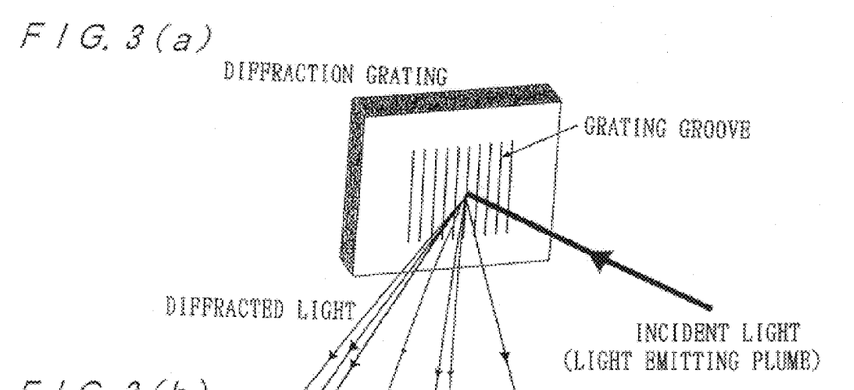
FIG. 3 shows a diagram, a photograph, and a graph which illustrate a spectroscopic image processing according to the present invention.
Figure 3B:
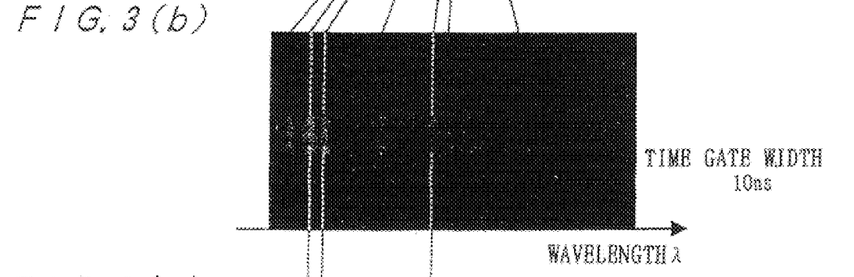
Figure 3C:
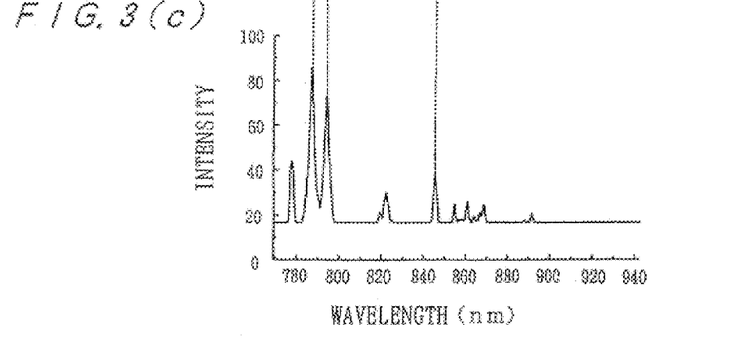

FIGS. 3(*a*), 3(*b*), and 3(*c*) are a diagram, a photograph, and a graph which illustrate spectroscopic image processing according to the present invention. FIG. 3(*a*) shows splitting of light effected by the gratings 16D–16F of the polychromator 16. FIG. 3(*b*) shows a spectroscopic image captured by the CCD camera 9. FIG. 3(*c*) shows a spectrum which is eventually obtained.

Since the light beam is not split vertically by the gratings 16D–16F, detected photons along a vertical line are of the same wavelength. Therefore, through integration in the vertical direction, a spectrum is obtained as shown in FIG. 3(*c*). Win View, a software application for spectral analysis, was used for this processing.

Calibration of a wavelength scale will now be described.

As described above, the light beams exiting from the polychromator 16 form images on the pixels of the CCD camera 9. For accurate measurement, calibration must be performed so as to establish proper correspondence between the images and wavelengths. In the present embodiment, a mercury lamp was used for calibration.

Figure 4A:
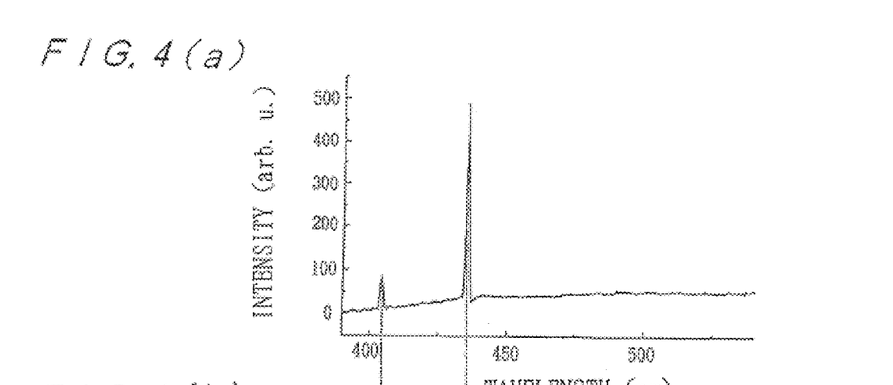
FIG. 4 shows a graph and photographs which illustrate a method for wavelength calibration according to the present invention.
Figure 4B:
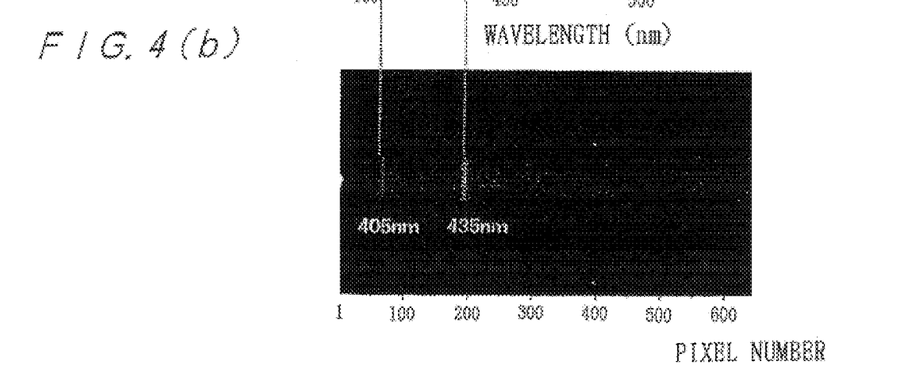
Figure 4C:
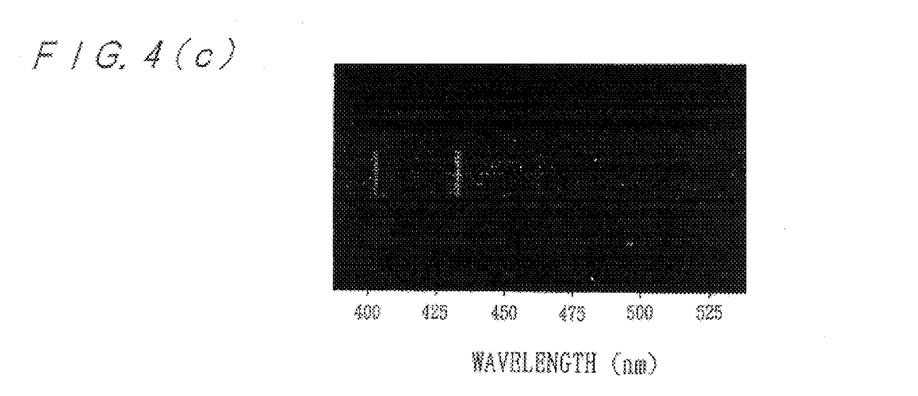

FIGS. 4(a), 4(b), and 4(c) are a graph and photographs which illustrate a method for wavelength calibration according to the present invention. FIG. 4(a) shows the spectrum of a mercury lamp, which is known. FIG. 4(b) shows a spectroscopic image of the mercury lamp. FIG. 4(c) shows a calibrated spectroscopic image of the mercury lamp.

First, as shown in FIG. 4(a), a light beam from the mercury-arc lamp is split, and a spectroscopic image thus obtained is captured, as shown in FIG. 4(b). Within the wavelength range shown in FIG. 4(a), two known emission lines of mercury are observed, at wavelengths of 405 and 435 nm. Calibration at all wavelengths within an intended wavelength range can be performed through an operation of causing the two wavelengths to correspond to the two emission lines observed in the spectroscopic image. Win.Spec., a software application for spectral analysis, was used for the calibration.

A pulse synchronization/delay system will now be described.

A synchronizing system is a very important factor in spectroscopic analysis performed on the order of nanosecond.

As shown in FIG. 1, the avalanche photo diode (APD) 5 was used for detection of an output laser pulse; and the output signal and the gate signal of the high-speed gate image intensifier 17 were monitored in a synchronized manner by use of the oscilloscope 6 in order to measure a delay time of the gate signal output from the pulse generator 8.

The gate width and delay time ($t_d$) of the high-speed gate image intensifier 17 are controlled by the pulse generator 8. The intensifier 17 and the CCD camera 9 are operated in synchronization with the Q-switched Nd:YAG laser 1.

Determination of the gate width of the high-speed gate image intensifier will now be described.

In order to determine a gate width $t_g$ suitable for spectroscopic analysis of emission spectra of a light emitting plume, the spectra were measured while the gate width of the high-speed gate image intensifier 17 was varied.

Figure 5A:
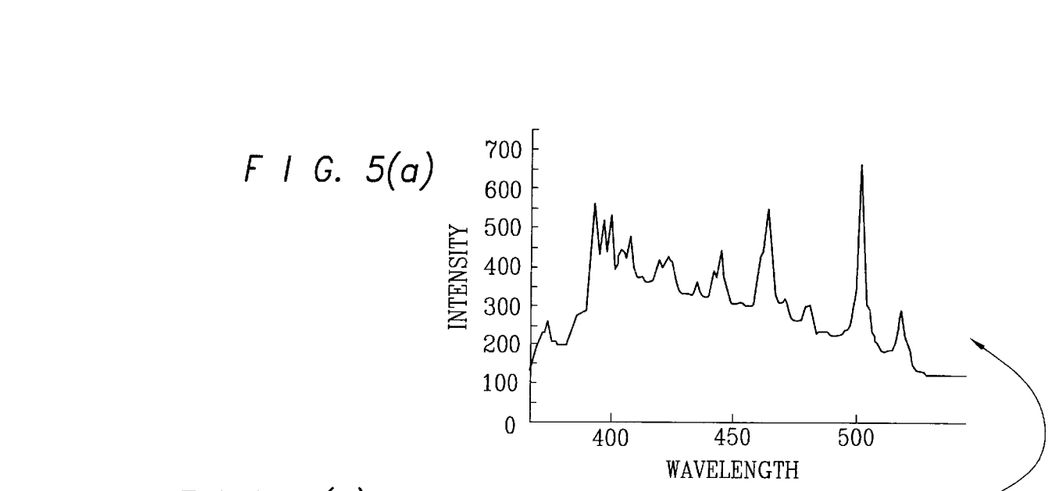
FIG. 5 shows graphs which illustrate results of measurement performed while the gate width of a high-speed gate image intensifier of the present invention is varied.
Figure 5B:
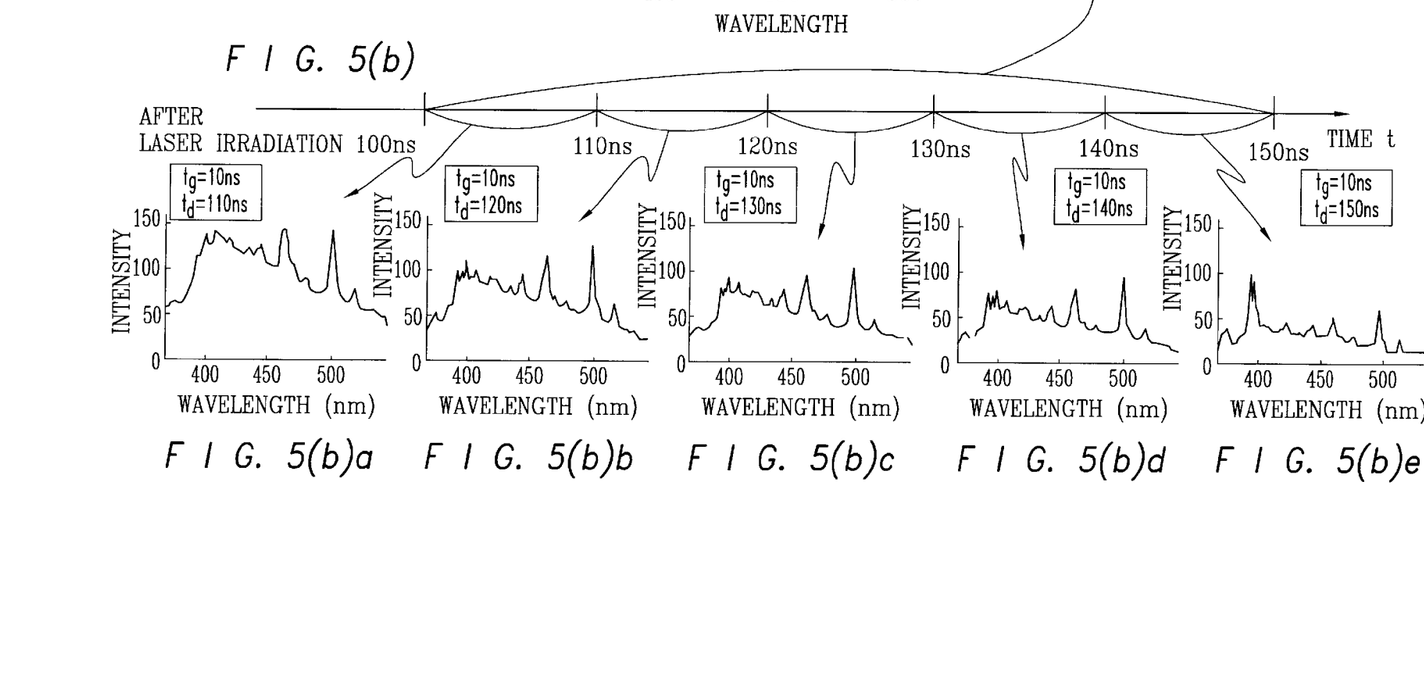

FIGS. 5 are graphs which illustrate results of measurement performed while the gate width of a high-speed gate image intensifier was varied. FIG. 5(a) shows a spectrum of a human tooth when the gate width was set to 50 ns and the delay time $t_d$ was set to 150 ns. FIG. 5(b) shows spectra of the human tooth when the gate width was set to 10 ns and the delay time was varied among 110 ns, 120 ns, 130 ns, 140 ns, and 150 ns.

The spectrum of FIG. 5(a) was obtained in the case where the gate width was 50 ns at the delay time of 150 ns after irradiation of the laser pulse. This image corresponds to the sum of five images which were obtained at the delay time of 110, 120, 130, 140 and 150 ns, respectively, where the gate width was 10 ns.

As is apparent from FIG. 5(a), some emission lines are observed in this measurement. However, as shown in FIG. 5(b), the spectra of the plume was found to change greatly between 100 ns and 150 ns after laser irradiation, through measurement in which spectra of the light emitting plume were measured at a gate width of 10 ns, while the delay time after laser irradiation was changed in five steps from 100 ns to 150 ns. That is, when the gate width was set to 10 ns, the emission line in the vicinity of 390 nm, which was not clearly defined when the gate width was set to 50 ns, due to the presence of other emission lines, was clearly observed up to the delay time $t_d$ of 150 ns.

Consequently, the gate width of 50 ns is not sufficient in terms of time resolution. Although the gate width can be shortened to 3 ns, this has the effect of decreasing the quantity of light. Therefore, the gate width was set to 10 ns.

The conditions for laser irradiation and the conditions for spectroscopic analysis will now be described.

The conditions for laser ablation and the nanosecond time-gate spectroscopic measurement according to the present invention are shown in the following table.

| Q-switched Nd:YAG laser | Wavelength | 1064, 532, and 266 nm |
|---|---|---|
| | Pulse width | 5–50 ns |
| | Pulse energy | 17 mJ |
| | Spot size at focal point | 50 μm |
| | Fluence | $8.7 \times 10^2$ J/cm$^2$ |
| Gate width of image intensifier | | 10 ns |
| Gain of image intensifier | | $2.9 \times 10^4$ |
| Measurement wavelength range | | 360–540 nm |

Exemplary conditions for spectroscopic measurement include a gate width—which indicate the time resolution of spectra of a light emitting plume—and a measurement wavelength range, which varies in accordance with the type of grating.

The gate width was set to 10 ns, and the measurement wavelength range was 180 nm, because a grating having a grating groove density of 300/mm was used.

As described above, the present invention enables instantaneous spectroscopic analysis of a light-emitting plume through irradiation of a biological tissue sample with a single laser pulse.

Further, irradiation of a biological tissue sample with a single laser pulse is enabled through disposition of a shutter between the light source and the sample.

In addition, since the high-speed gate image intensifier is synchronized with the CCD camera by use of a trigger pulse of the Q-switched Nd:YAG laser, light emission caused by laser ablation and capture of a spectroscopic image obtained therefrom can be synchronized.

Specific examples of the present invention will next be described.

A nanosecond time-gate spectroscopic analysis of laser ablation of biological tissue was performed. Further, in order to observe changes in biological tissue after laser ablation, microphotographs were taken.

(1) Variation with Time of a Light-Emitting Plume

When a laser beam emitted from the Q-switched Nd:YAG laser (fundamental wavelength λ=1064 nm) was radiated onto a human tooth, two plumes having different growth rates in air (leading and chasing plumes) were observed through stroboscopic microscopy. In order to separate these two plumes with respect to time, variations with time of the emission spectra of the plumes of the human nail were first measured.

Figure 6A:
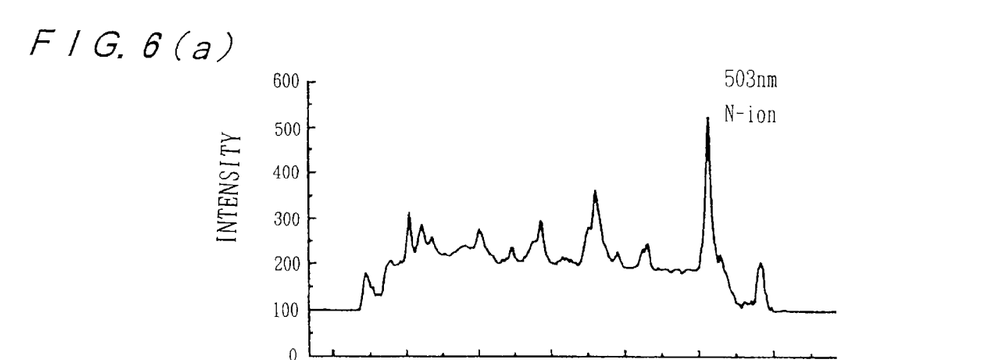
FIG. 6 shows graphs illustrating the results of a measurement performed in a first example of the present invention in order to measure variation with time of a light emitting plume generated from a human nail.
Figure 6B:
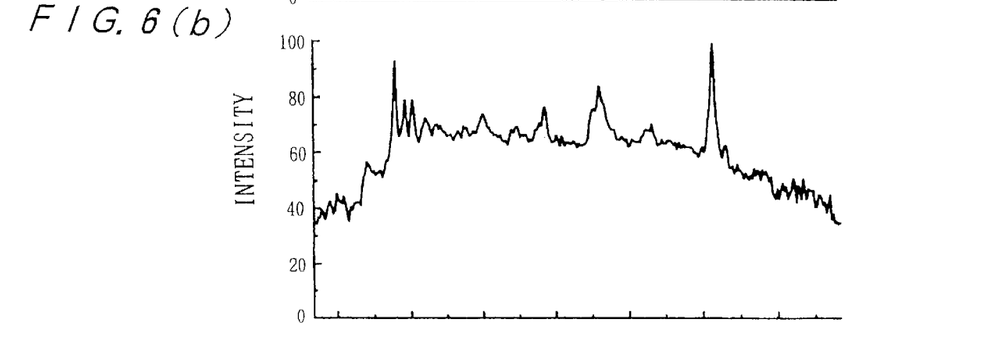
Figure 6C:
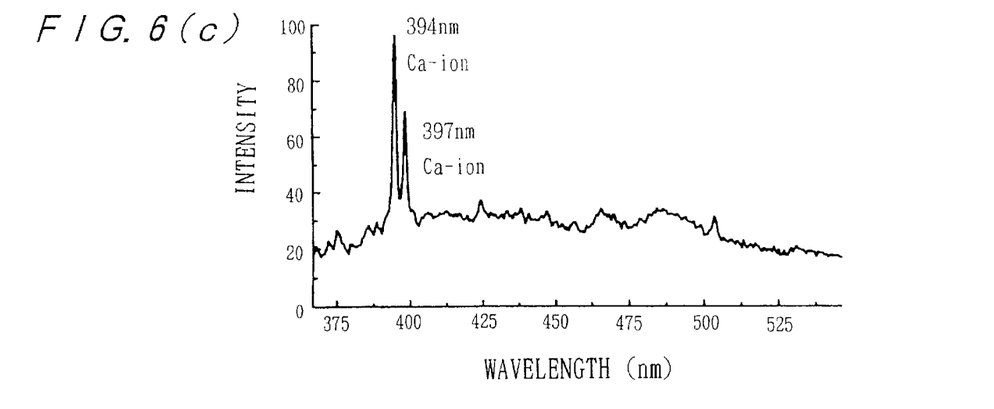

FIGS. 6(a), 6(b), and 6(c) are graphs illustrating the results of a measurement performed in a first embodiment of the present invention in order to measure variations with time of a light emission plume generated from the human nail. FIG. 6(a), FIG. 6(b), and FIG. 6(c) show emission spectra at delay times ($t_d$) of 200 ns, 300 ns, and 400 ns, respectively. In all cases, the laser pulse width was set to 35 ns, the gate width of the high-speed gate image intensifier was set to 10 ns, and pulse energy was 17 mJ.

In FIG. 6(a), when the delay time is 200 ns (i.e. at 200 ns after laser irradiation), a strong emission line is observed in the vicinity of a wavelength of 500 nm.

However, as is apparent from FIGS. 6(b) and 6(c), the emission line gradually decreases as $t_d$ is increased to 300 ns and 400 ns, and therefore the line is considered to be the emission line of nitrogen (N), which is a component of the leading plume of the human nail.

In contrast, in the vicinity of a wavelength of 390 nm, there is observed an emission line which begins to grow as $t_d$ is increased to 300 ns. The line corresponds to an emission spectrum of calcium (Ca) which is contained in the chasing plume of the human nail. Thus, after $t_d$ is increased beyond 300 ns, the effect of the leading plume on the spectrum drastically decreases, and the chasing plume, which reflects the components of the biological tissue, strongly affects the spectrum. Therefore, the composition of the biological tissue can be analyzed on the basis of the results of time-gate spectroscopic analysis.

(2) Spectroscopic Analysis of Light Emitting Plume

Figure 7:
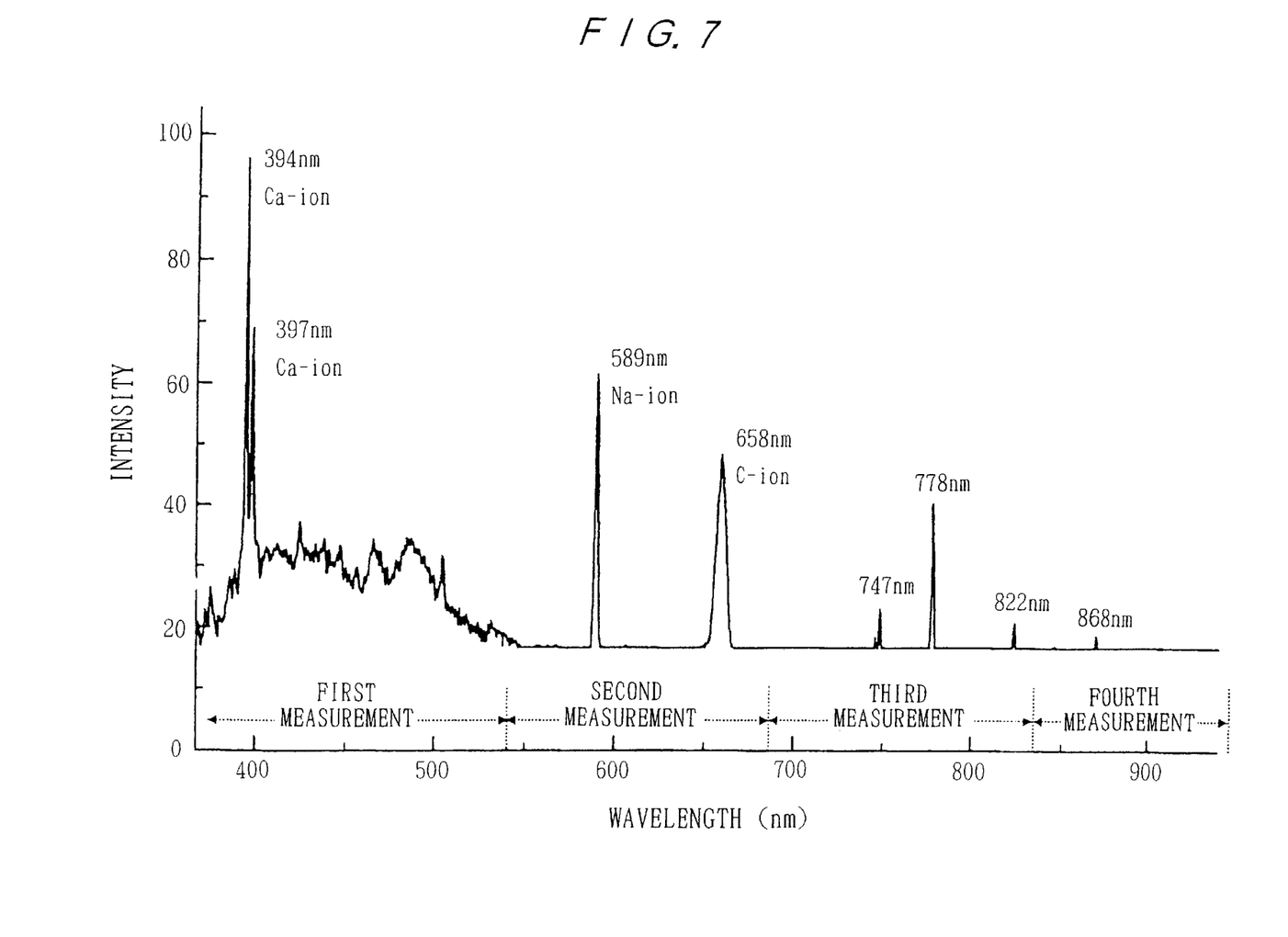
FIG. 7 is a graph showing the results of an analysis performed in the first example of the present invention in order to analyze a light emitting plume generated from a human nail.

FIG. 7 is a graph showing the results of an analysis performed in the first example of the present invention in order to analyze a light emitting plume generated from a human nail. In this case, the laser pulse width was set to 35 ns, the gate width of the high-speed gate image intensifier was set to 10 ns, and the pulse energy was 17 mJ.

As shown in FIG. 7, analysis was performed at a delay time ($t_d$) of 400 ns in order to determine the components of the chasing plume of the human nail. A range that can be measured by irradiation of a single laser pulse is 180 nm, and therefore measurement was performed four times, to thereby obtain a spectrum having a range of 380 to 900 nm.

In the spectrum, two strong emission lines are observed in the vicinity of 390 nm, and these are emission lines of calcium (Ca). In the spectrum, other two emission lines are observed at 589 nm and 658 nm, which are presumed to correspond to sodium (Na) and carbon (C), respectively. The remaining peaks, which are considered to correspond to calcium (Ca), oxygen (O), and phosphoric acid (HPO), are observed, but their identification is difficult, because emission lines of various elements are present in the vicinity of each of these peaks.

In addition, over a range of 400–500 nm in the spectrum, a broad absorption spectrum is observed but cannot be identified. Henceforth, the spectrum should be studied, because some organic compounds are considered to have similar absorption spectra.

The content of Ca in the human nail is approximately 0.1%. However, the intensity of the emission line of Ca was confirmed to be stronger than that of carbon (C) constituting keratin, which is a primary component of the human nail. From the results, the present measurement system was found to have very high sensitivity with respect to calcium (Ca). In view of the foregoing, a variety of biological tissues were analyzed spectroscopically by use of emission lines of calcium.

The results of spectroscopic analysis performed for a variety of biological tissues will now be described.

(1) Results of Analysis of Human Hair

Figure 8:
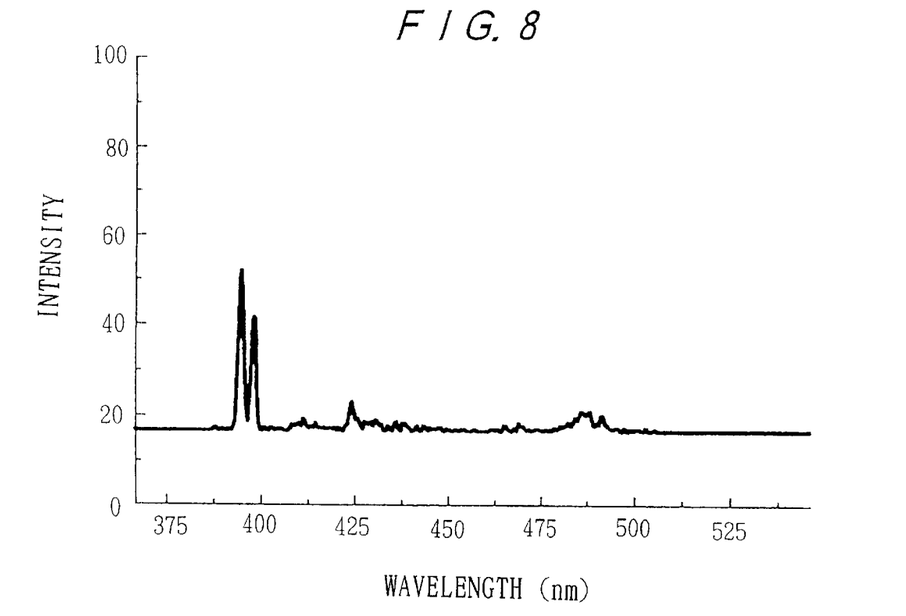
FIG. 8 is a graph showing the results of an analysis performed in a second example of the present invention in order to analyze a light emitting plume generated from human hair.

FIG. 8 is a graph showing the results of an analysis performed in a second example of the present invention in order to analyze a light emitting plume generated from human hair. In this case, the laser pulse width was set to 35 ns, the gate width of the high-speed gate image intensifier was set to 10 ns, and the pulse energy was 17 mJ.

As shown in FIG. 8, measurement was performed at a delay time $t_d$ of 400 ns. The content of Ca in human hair is approximately 0.1%, but the emission line of Ca was apparently observed. Measurement could be performed through use of a single hair shaft, since the diameter of the laser beam at a focal point is small as 50 $\mu$m. Since the Ca content of hair reflects that in the body, the analysis is expected to be applied to medical diagnosis.

(2) Results of Analysis of a Human Tooth

Figure 9:
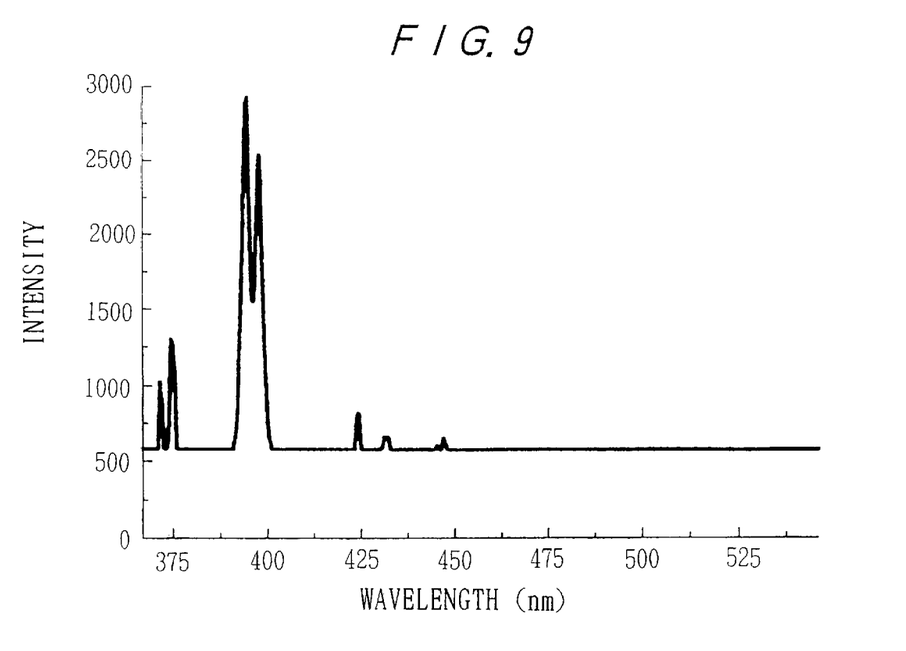
FIG. 9 is a graph showing the results of an analysis performed in a third example of the present invention in order to analyze a light emitting plume generated from a human tooth.

FIG. 9 is a graph showing the results of an analysis performed in a third example of the present invention in order to analyze a light emitting plume generated from a human tooth. In this case, the laser pulse width was set to 35 ns, the gate width of the high-speed intensifier image was set to 10 ns, and the pulse energy was 17 mJ.

As shown in FIG. 9, measurement was performed at a delay time $t_d$ of 400 ns. In the case of the tooth, as is apparent from the Figure, the emission line of Ca has very high intensity as compared with the cases of the nail and the hair, since the calcium content of the tooth (enamel) is 36%.

(3) Results of Spectroscopic Analysis of Chicken Skin

Figure 10:
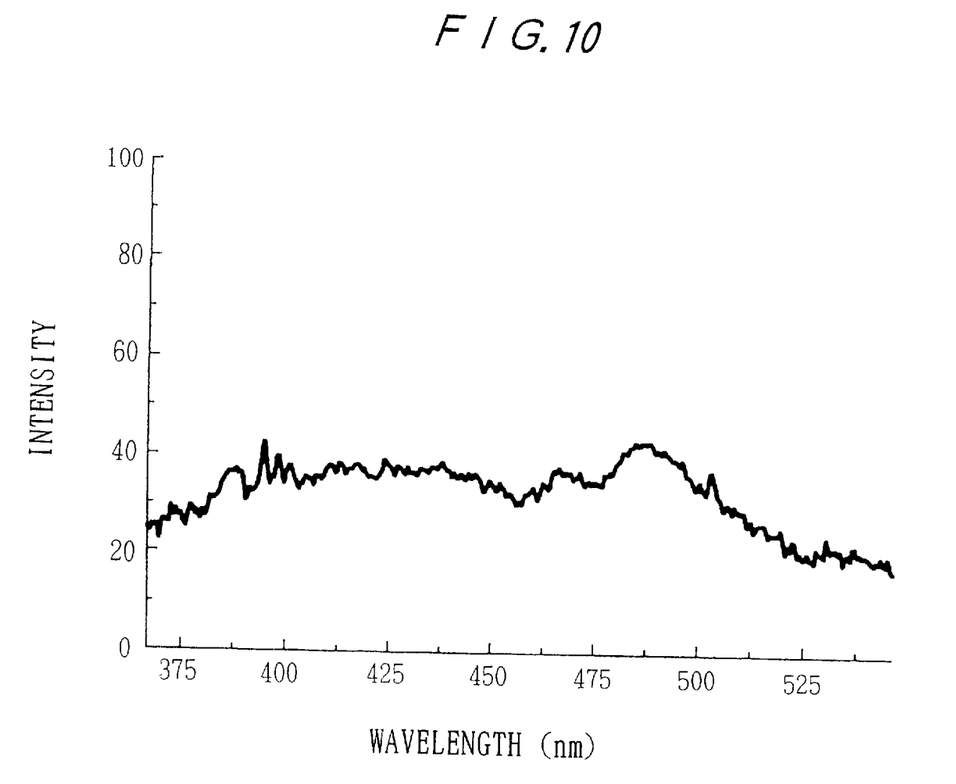
FIG. 10 is a graph showing the results of an analysis performed in a fourth example of the present invention in order to analyze a light emitting plume generated from chicken skin.

FIG. 10 is a graph showing the results of an analysis performed in a fourth example of the present invention in order to analyze a light emitting plume generated from chicken skin. In this case, the laser pulse width was set to 35 ns, the gate width of the high-speed gate image intensifier was set to 10 ns, and the pulse energy was 17 mJ.

As shown in FIG. 10, measurement was performed at a delay time $t_d$ of 400 ns. The peak corresponding to Ca was hardly observed, since the calcium content of chicken skin is very low. Meanwhile, over the entire range of 360–540 nm, a broad peak similar to an absorption spectrum was observed. The broad peak is presumed to be attributable to organic compounds, as is described in the above spectroscopic analysis of light-emitting plumes.

As described above, in the nanosecond time-gate spectroscopic system of the present invention, biological tissue was analyzed spectroscopically on the basis of a light-emitting plume generated by laser ablation, by use of a laser beam emitted from the Q-switched Nd:YAG laser and having a fundamental wave of 1064 nm.

As a result, an emission line corresponding to calcium in the biological tissue could be found with high sensitivity. The present inventors presume that the intensity of a calcium emission line corresponds to the calcium content of the biological tissue, and this phenomenon enables optical clinical diagnosis. For example, an emission line of calcium (Ca) apparently observed as described above can serve as the basis for diagnosis of osteoporosis, and the degree of aging may be determined thereby. Further, diagnosis of heavy metal poisoning may be performed through spectroscopic analysis of hair.

The present invention provides the following effects:

(1) In the nanosecond time-gate spectroscopic diagnosis apparatus described in (1) above, spectroscopic analysis of a light-emitting plume of an evaporated substance can be easily performed through irradiation of a biological tissue sample with a single laser pulse, and optical diagnosis can be performed instantaneously in a substantially noninvasive manner.

Further, a minute amount of ions of a metal such as Ca, Na, or K, which have a high ionization tendency, can be effectively detected through spectroscopic analysis of a chasing plume generated from the surface of biological tissue.

(2) In the nanosecond time-gate spectroscopic diagnosis apparatus described in (2) above, spectroscopic analysis of a light-emitting plume of an evaporated substance can be performed quickly and reliably.

(3) In the nanosecond time-gate spectroscopic diagnosis apparatus described in (3) above, spectroscopic analysis of a light-emitting plume of an evaporated substance can be performed quickly and reliably by use of a multi-purpose light source.

(4) In the nanosecond time-gate spectroscopic diagnosis apparatus described in (4) above, the size of the diagnosis apparatus can be reduced.

(5) In the nanosecond time-gate spectroscopic diagnosis apparatus described in (5) above, unlike the case of a conventional fluorescence diagnosis, a laser beam emitted from the light source is not required to have a wavelength shorter than that of a light-emitting plume to be detected.

(6) In the nanosecond time-gate spectroscopic diagnosis apparatus described in (6) above, spectroscopic diagnosis can be performed accurately through irradiation of a biological tissue sample with a single laser pulse, while the level of invasiveness is reduced to a considerably low level.

(7) In the nanosecond time-gate spectroscopic diagnosis apparatus described in (7) above, light components corresponding to different wavelengths within a predetermined range are caused to exit from an exit opening simultaneously at different angles, so that light splitting can be performed for each wavelength.

(8) In the nanosecond time-gate spectroscopic diagnosis apparatus described in (8) above, resolution can be adjusted through variation in the density of grating grooves.

(9) In the nanosecond time-gate spectroscopic diagnosis apparatus described in (9) above, light output from the high-speed gate image intensifier can be caused to form an image on the pixels of the CCD camera.

(10) In the nanosecond time-gate spectroscopic diagnosis apparatus described in (10) above, the high-speed gate image intensifier and the CCD camera can be synchronized with a trigger pulse from the light source in order to reliably yield a spectroscopic image.

(11) In the nanosecond time-gate spectroscopic diagnosis apparatus described in (11) above, through laser ablation of biological hard tissue such as hair, a nail, or a tooth, the content of Ca can be determined in order to diagnose osteoporosis.

(12) In the nanosecond time-gate spectroscopic diagnosis apparatus described in (12) above, through laser ablation of biological soft tissue such as a vascular wall or subepidermal tissue, the content of, for example, an organic compound can be determined in order to perform noninvasive optical diagnosis.

The present invention is not limited to the above-describe embodiments. Numerous modifications and variations of the present invention are possible in light of the spirit of the present invention, and they are not excluded from the scope of the present invention.

INDUSTRIAL APPLICABILITY

As described above, a nanosecond time-gate spectroscopic diagnosis apparatus according to the present invention is suitable to diagnosis, in which a laser pulse from a light source is radiated onto biological tissue in a focused manner, a light emitting plume generated from the surface of the tissue due to laser ablation is spectroscopically measured at a time gate on the order of nanosecond, and the composition of the tissue is analyzed on the basis of the plume spectra, to thereby diagnose lesion and anomaly of the biological tissue.

What is claimed is:

1. A nanosecond time-gate spectroscopic diagnosis apparatus wherein a laser pulse from a light source illuminates biological tissue in a focused manner, a light emitting plume generated from the surface of the tissue due to laser ablation is spectroscopically measured at a time gate on the order of nanosecond, and the composition of the tissue is analyzed on the basis of the plume spectra, to thereby diagnose a lesion or anomaly of the tissue, the apparatus comprising:

(a) a shutter, disposed between the light source and a lens opposed to the biological tissue, for irradiating the biological tissue with a single laser pulse while minimizing invasion of the biological tissue;

(b) a multi-channel spectrometer (polychromator) for detecting a light emitting plume generated by the single laser pulse;

(c) a photodetector for detecting a portion of the laser pulse from the light source;

(d) an oscilloscope which monitors an output from the photodetector to thereby measure a delay time of a gate trigger pulse supplied to a high-speed gate image intensifier;

(e) a pulse generator cable for independently and freely adjusting the delay times of two output pulses in synchronization with the illuminating laser pulse;

(f) a gate controller connected to the pulse generator and the oscilloscope;

(g) the high-speed gate image intensifier intensifying and imaging the output of the multi-channel spectrometer whose gate is opened by the gate controller over a period on the order of nanosecond;

(h) a CCD camera capturing an output image from the high-speed gate image intensifier; and (i) a data-processing apparatus comprising frame image data storage which inputs spectroscopic image data of one frame from the CCD camera as a time-series analog signal, and converts the analog signal to a digital signal for transmission to a computer.

2. A nanosecond time-gate spectroscopic diagnosis apparatus according to claim 1, wherein biological tissue is evaporated and excited by laser ablation, and spectra of a light emitting plume generated due to evaporation and excitation are detected at intervals on the order of nanosecond.

3. A nanosecond time-gate spectroscopic diagnosis apparatus according to claim 1, wherein the light source is a laser light source which generates a nanosecond laser pulse within the UV range, the visible range, or the IR range.

4. A nanosecond time-gate spectroscopic diagnosis apparatus according to claim 1, wherein the laser beam source is a flash-lamp-excited or semiconductor-laser-excited Q-switched Nd:YAG laser, or a semiconductor-laser-excited full-solid Q-switched Nd:YAG laser.

5. A nanosecond time-gate spectroscopic diagnosis apparatus according to claim 1, wherein a laser beam from the light source includes light having a wavelength longer than the wavelength of the light emitting plume to be detected.

6. A nanosecond time-gate spectroscopic diagnosis apparatus according to claim 1, wherein the multi-channel spectrometer has a structure such that a light beam entering through an inlet slit is split, by use of a plurality of gratings, into a plurality of light beams corresponding to different wavelengths, and light beams having wavelengths within a particular range exit simultaneously from an exit opening at different angles.

7. A nanosecond time-gate spectroscopic diagnosis apparatus according to claim 6, wherein the density of grating grooves of the grating is selectively set to 150/mm, 300/mm, 600/mm, or 1200/mm.

8. A nanosecond time-gate spectroscopic diagnosis apparatus according to claim 6, wherein light beams having wavelengths within a particular range and exiting from the multi-channel spectrometer forms an image on pixels of the CCD camera.

9. A nanosecond time-gate spectroscopic diagnosis apparatus according to claim 1, further comprising means for synchronizing operation of the high-speed gate image intensifier and operation of the CCD camera with a trigger pulse from the light source.

10. A nanosecond time-gate spectroscopic diagnosis apparatus according to claim 1, wherein the biological tissue is biological hard tissue such as hair, a nail, or a tooth.

11. A nanosecond time-gate spectroscopic diagnosis apparatus according to claim 1, wherein the biological tissue is biological soft tissue such as a vascular wall or subepidermal tissue.

* * * * *